(12) United States Patent
Takahashi et al.

(10) Patent No.: US 11,097,997 B2
(45) Date of Patent: Aug. 24, 2021

(54) METHOD FOR PRODUCING HEXAFLUOROBUTADIENE

(71) Applicant: DAIKIN INDUSTRIES, LTD., Osaka (JP)

(72) Inventors: Kazuhiro Takahashi, Osaka (JP); Yuuko Ohhigashi, Osaka (JP); Junpei Iyota, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 16/757,501

(22) PCT Filed: Oct. 23, 2018

(86) PCT No.: PCT/JP2018/039293
§ 371 (c)(1),
(2) Date: Apr. 20, 2020

(87) PCT Pub. No.: WO2019/082872
PCT Pub. Date: May 2, 2019

(65) Prior Publication Data
US 2020/0247735 A1    Aug. 6, 2020

(30) Foreign Application Priority Data
Oct. 23, 2017   (JP) .............................. JP2017-204335

(51) Int. Cl.
C07C 17/386    (2006.01)
C07C 21/20    (2006.01)

(52) U.S. Cl.
CPC ............ *C07C 17/386* (2013.01); *C07C 21/20* (2013.01)

(58) Field of Classification Search
CPC ........ C07C 17/386; C07C 21/20; C07C 21/18
See application file for complete search history.

(56) References Cited

U.S. PATENT DOCUMENTS 4,654,448 A    3/1987    Bargigia et al.
2002/0193643 A1    12/2002    Miki et al.

FOREIGN PATENT DOCUMENTS

| CN | 107032949 | 8/2017 |
|---|---|---|
| JP | 62-26240 | 2/1987 |
| JP | 11-43451 | 2/1999 |
| JP | 2001-192345 | 7/2001 |

OTHER PUBLICATIONS

International Search Report dated Dec. 18, 2018 in International (PCT) Application No. PCT/JP2018/039293.
Extended European Search Report dated Jun. 29, 2021, in corresponding European Patent Application No. 18871178.2.

*Primary Examiner* — Jafar F Parsa
(74) *Attorney, Agent, or Firm* — Wenderoth, Lind & Ponack, L.L.P.

(57) ABSTRACT

By subjecting a starting material composition containing hexafluorobutadiene and at least one additional compound selected from the group consisting of octafluoro-1-butene, octafluoro-2-butene, heptafluoro-1-butene, and heptafluoro-2-butene to extractive distillation in the presence of an extraction solvent to reduce the concentration of the additional compound, hexafluorobutadiene with higher purity can be obtained.

8 Claims, 1 Drawing Sheet

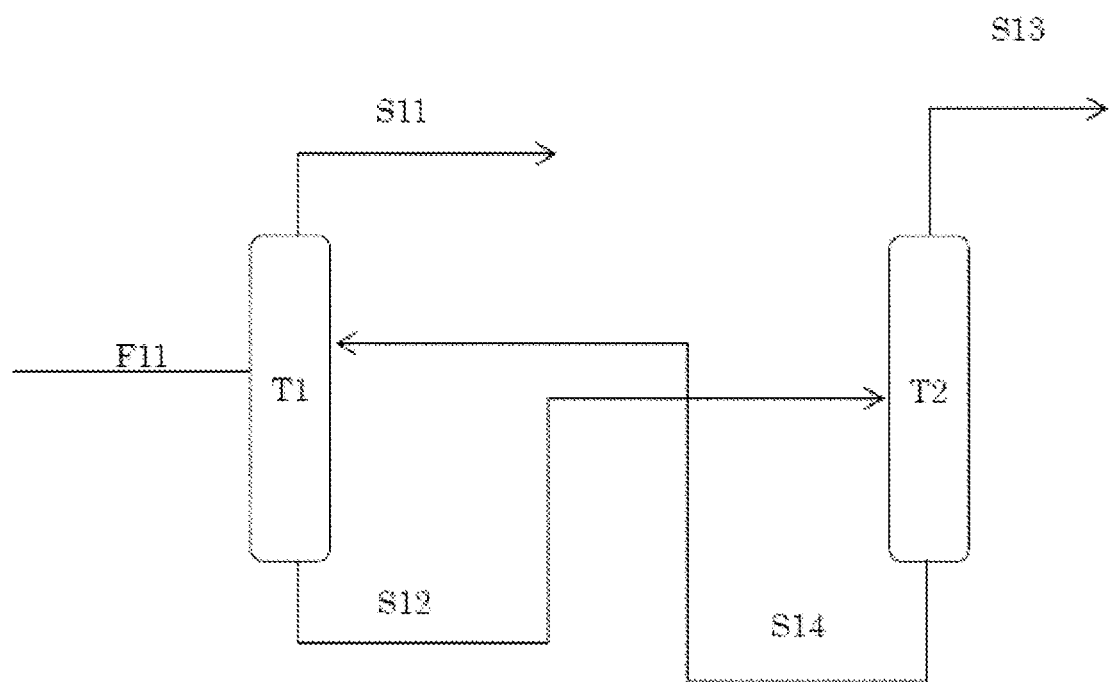

METHOD FOR PRODUCING HEXAFLUOROBUTADIENE

TECHNICAL FIELD

The present invention relates to a method for producing hexafluorobutadiene.

BACKGROUND ART

Miniaturization and the use of new materials for semiconductor devices have been studied for the purpose of acceleration and energy-saving. Fluorocarbons are known to be suitable for the microfabrication of semiconductor devices. Of these, hexafluorobutadiene ($CF_2$=CFCF=$CF_2$, 1,1,2,3,4,4-hexafluorobutadiene, etc.) is attracting attention as an etching gas used for forming state-of-the-art microstructures, such as semiconductors and liquid crystals.

It is necessary to reduce impurities in a dry etching gas as much as possible in order to increase the yield. The purity of a gas used for dry etching is generally as high as 99.99% (4N) or 99.999% (5N). On the other hand, as a method for producing hexafluorobutadiene, a dehalogenation reaction, for example, in which a corresponding halide is reacted with zinc metal, is known (for example, see Patent Literature 1).

CITATION LIST

Patent Literature

PTL 1: No. 1987-26240

SUMMARY OF INVENTION

Technical Problem

However, hexafluorobutadiene purified by the reaction described in Patent Literature 1 includes, as additional compounds, octafluoro-1-butene, octafluoro-2-butene, heptafluoro-1-butene, hebutafluoro-2-butene, and the like.

Hexafluorobutadiene has a structure and a boiling point similar to those of the additional compounds. For this reason, separation by a normal distillation method is difficult, and a method for obtaining hexafluorobutadiene with high purity is desired.

The present invention has been made to solve the above problem, and aims to provide a method for obtaining hexafluorobutadiene with high purity.

Solution to Problem

As a result of extensive research to solve the above problem, the present inventors accomplished the present invention. The present invention includes the following structure.

Item 1. A method for producing hexafluorobutadiene, comprising a step of subjecting a starting material composition containing hexafluorobutadiene and at least one additional compound selected from the group consisting of octafluoro-1-butene, octafluoro-2-butene, heptafluoro-1-butene, and heptafluoro-2-butene to extractive distillation in the presence of an extraction solvent to reduce the concentration of the additional compound.

Item 2. The production method according to Item 1, wherein the extraction solvent used in the extractive distillation is at least one solvent selected from the group consisting of oxygen-containing hydrocarbons and halogen-containing hydrocarbons.

Item 3. A method for separating hexafluorobutadiene and at least one additional compound selected from the group consisting of octafluoro-1-butene, octafluoro-2-butene, heptafluoro-1-butene, and heptafluoro-2-butene, the method comprising a step of subjecting a composition containing hexafluorobutadiene and the additional compound to extractive distillation in the presence of an extraction solvent.

Item 4. The method according to Item 3, wherein the extraction solvent contains at least one compound selected from the group consisting of oxygen-containing hydrocarbons and halogen-containing hydrocarbons.

Item 5. A composition containing hexafluorobutadiene and at least one additional compound selected from the group consisting of octafluoro-1-butene, octafluoro-2-butene, heptafluoro-1-butene, and heptafluoro-2-butene, wherein the additional compound is contained in an amount of less than 0.1 mol % per 100 mol % of the total amount of the composition.

Item 6. An azeotropic composition containing hexafluorobutadiene and at least one additional compound selected from the group consisting of octafluoro-1-butene, octafluoro-2-butene, heptafluoro-1-butene, and heptafluoro-2-butene.

Item 7. The composition according to Item 5 or 6, for use in an etching gas, a refrigerant, a heat transfer medium, a foaming agent, or a resin monomer.

Advantageous Effects of Invention

According to the present invention, hexafluorobutadiene with high purity can be obtained.

BRIEF DESCRIPTION OF DRAWINGS

FIG. 1 shows an example of an apparatus for performing the separation method (the method for producing hexafluorobutadiene) of the present invention.

DESCRIPTION OF EMBODIMENTS

The present invention is a production method for obtaining hexafluorobutadiene with a higher concentration from a composition containing hexafluorobutadiene and at least one additional compound selected from the group consisting of octafluoro-1-butene, octafluoro-2-butene, heptafluoro-1-butene, and heptafluoro-2-butene, wherein the method includes the step of subjecting the composition to extractive distillation in the presence of an extraction solvent to reduce the concentration of the additional compound.

Since hexafluorobutadiene has a structure and a boiling point similar to those of the additional compounds, the separation thereof by a normal distillation method is difficult. For example, the boiling point of hexafluorobutadiene is 6° C., while the boiling points of octafluoro-1-butene, octafluoro-2-butene, heptafluoro-1-butene, and heptafluoro-2-butene are respectively 4° C., 1.2° C., 20° C., and 8° C. To separate these substances by normal distillation, a distillation column having many plates is required, and separation is substantially impossible. Even if separation is possible, a large amount of loss is incurred, which is economically inefficient. In contrast, in the present invention, the concentration of the additional compound can be reduced by extractive distillation, and hexafluorobutadiene having a high concentration can be obtained.

Starting Material Composition

The starting material composition contains hexafluorobutadiene and at least one additional compound selected from the group consisting of octafluoro-1-butene ($CF_2$=$CFCF_2CF_3$), octafluoro-2-butene ($CF_3CF$=$CFCF_3$), heptafluoro-1-butene ($CF_2$=$CFCF_2CF_2H$, $CF_2$=$CFCFHCF_3$, $CF_2$=$CHCF_2CF_3$, $CFH$=$CFCF_2CF_3$, etc.) and heptafluoro-2-butene ($CF_3CF$=$CFCF_2H$, $CF_3CF$=$CHCF_3$, etc.).

Such a starting material composition can be produced by a method conventionally known as a method for producing hexafluorobutadiene. The staring material composition can also be synthesized by other methods.

In one example of the other methods, synthesis can be performed by a method including a reaction step of adding a nitrogen-containing compound to a solution of a compound represented by formula (1):

$$X^1CF_2\text{—}CFX^2\text{—}CF_2\text{—}CF_2X^1 \qquad (1)$$

wherein $X^1$s may be the same or different, and each represents a halogen atom other than fluorine; and $X^2$ represents a halogen atom.

In formula (1), $X^1$ is a halogen atom other than fluorine; and examples include chlorine, bromine, iodine, and the like. Of these, chlorine or iodine is preferable from the viewpoint of obtaining hexafluorobutadiene with a higher yield. $X^1$s may be the same or different.

In formula (1), $X^2$ is a halogen atom; and examples include fluorine, chlorine, bromine, iodine, and the like. Of these, from the viewpoint of obtaining hexafluorobutadiene with a higher yield, fluorine or chlorine is preferable, and chlorine is more preferable.

Examples of the compound represented by formula (1) that satisfies the above conditions include $ClCF_2$—$CFCl$—$CF_2$—$CF_2I$, $ICF_2$—$CF_2$—$CF_2$—$CF_2I$, and the like. From the viewpoint of obtaining hexafluorobutadiene with a higher yield, $ClCF_2$—$CFCl$—$CF_2$—$CF_2I$ is preferable.

In this production method, for example, a nitrogen-containing compound (an amide compound, such as N,N-dimethylformamide and N,N-diisopropylformamide; an amine compound, such as triethylamine; a pyridine compound, such as pyridine, methylpyridine, N-methyl-2-pyrrolidone; a quinoline compound, such as quinoline and methylquinoline; etc.) is added to a solution of a compound represented by formula (1) in a nonpolar organic solvent, such as heptane, hexane, benzene, toluene, or xylene, to promote the reaction. As the nitrogen-containing compound, those that are liquid at a normal temperature are included; however, use of the compound (in a small amount) as an additive rather than a solvent is preferable to obtain hexafluorobutadiene with a higher yield. The other reaction conditions are appropriately determined according to a normal method.

Thus, when hexafluorobutadiene is obtained by the conventional production method or the above production method, additional compounds such as octafluoro-1-butene ($CF_2$=$CFCF_2CF_3$), octafluoro-2-butene ($CF_3CF$=$CFCF_3$), heptafluoro-1-butene ($CF_2$=$CFCF_2CF_2H$, $CF_2$=$CFCFHCF_3$, $CF_2$=$CHCF_2CF_3$, $CFH$=$CFCF_2CF_3$, etc.), and heptafluoro-2-butene ($CF_3CF$=$CFCF_2H$, $CF_3CF$=$CHCF_3$, etc.) can also be produced as side products. Since hexafluorobutadiene and these additional compounds have a similar boiling point and a similar structure, it is difficult to separate them by normal distillation or the like. In particular, since the boiling point of hexafluorobutadiene is very close to that of heptafluoro-2-butene, separation of these is extremely difficult. Although the composition ratio of each component is not limited, when the starting material composition is produced by the conventional production method as described above, a composition containing hexafluorobutadiene in an amount of 73 to 99.9 mol % and additional compounds in an amount of 0.1 to 27 mol % per 100 mol % of the entire starting material composition is obtained in many cases. The above range is preferable as a composition to be separated by extractive distillation.

Extractive Distillation

In the present invention, the starting material composition is subjected to extractive distillation. This allows hexafluorobutadiene to be separated from octafluoro-1-butene, octafluoro-2-butene, heptafluoro-1-butene, heptafluoro-2-butene, or the like, each having a boiling point close to that of hexafluorobutadiene, and hexafluorobutadiene with higher purity can be obtained.

Since such separation is possible, octafluoro-1-butene, octafluoro-2-butene, heptafluoro-1-butene, or heptafluoro-2-butene, which is an additional compound, can be used in other reactions. Similar to hexafluorobutadiene, additional compounds can be efficiently used for various purposes, including etching gases for forming state-of-the-art microstructures such as semiconductors and liquid crystals; refrigerants; heat transfer media; foaming agents; resin monomers; etc.

Extractive distillation can be achieved by increasing or decreasing the relative volatility of both components (hexafluorobutadiene and additional compound) from 1. In this case, the further the relative volatility is from 1, the easier the separation of the hexafluorobutadiene and the additional compound by extractive distillation. When the relative volatility is 1, the composition of each phase becomes the same, which prevents separation by distillation.

Relative volatility is defined as the ratio of the equilibrium coefficients of components in a fluid mixture. If the components are hexafluorobutadiene (A) and an additional compound (B), the relative volatility (A/B) of hexafluorobutadiene (A) to the additional compound (B) is represented by the following equation.

$$\text{Relative volatility}(A/B)=X/Y$$

X indicates (gas phase mole fraction/liquid phase mole fraction) involving A.

Y represents (gas phase mole fraction/liquid phase mole fraction) involving B.

When hexafluorobutadiene is distilled off, it is usually preferable to use an extraction solvent having a relative volatility of greater than 1, particularly in the range of 1.10 to 2.00. When the relative volatility is greater than 1, the gas phase mole fraction of hexafluorobutadiene increases. This increases hexafluorobutadiene in the gas phase, allowing separation by distillation.

In contrast, when the additional compound is distilled off, it is preferable to use an extraction solvent having a relative volatility of less than 1, particularly in the range of 0.10 to 0.90. When the relative volatility is less than 1, the liquid phase mole fraction of hexafluorobutadiene increases. This increases hexafluorobutadiene in the liquid phase, allowing the distillation of the additional compound.

In the present invention, it is preferable to use an extraction solvent that can easily separate hexafluorobutadiene from the additional compound.

In the present invention, oxygen-containing hydrocarbons (alcohols, ketones, ethers, etc.), halogen-containing hydrocarbons (halogenated saturated hydrocarbons, halogenated unsaturated hydrocarbons, etc.), and the like can be used as extraction solvents.

Examples of alcohols include methanol, ethanol, n-propanol, isopropanol, n-butanol, tert-butyl alcohol, and the like. Of these, methanol and ethanol are preferred from the viewpoint of relative volatility.

Examples of ketones include acetone, methyl ethyl Ketone, diethyl ketone, methyl isobutyl ketone, and the like. Of these, methyl ethyl ketone is preferred from the viewpoint of relative volatility.

Examples of ethers include dialkyl ethers, such as dimethyl ether, methyl ethyl ether, and diethyl ether; ethylene glycol monoalkyl ethers, such as ethylene glycol monomethyl ether, ethylene glycol monoethyl ether, and ethylene glycol monobutyl ether; ethylene glycol dialkyl ethers, such as ethylene glycol dimethyl ether, ethylene glycol diethyl ether, and ethylene glycol dibutyl ether; and the like. From the viewpoint of relative volatility, ethylene glycol monoalkyl ethers are preferable, and ethylene glycol monomethyl ether is more preferable.

Examples of halogenated saturated hydrocarbons include 1,1,1-trifluoro-2,2-dichloroethane (HCFC-123), and the like.

Examples of halogenated unsaturated hydrocarbons include trichloroethylene, tetrachloroethylene (perchloroethylene), and the like.

These extraction solvents can be used alone, or in a mixture of two or more.

A water-soluble extraction solvent can be mixed with water, and used as an extraction solvent. For example, an aqueous solution of acetone, methanol, or the like can be used. The mixing ratio of the organic compound and water is preferably such that water is contained in an amount of less than 50 mass % in the extraction solvent, from the viewpoint of extraction efficiency. When the amount of water in the organic compound (solvent) is increased, the boiling point of the solvent composition becomes high, causing problems such as poor energy efficiency.

Regarding the temperature range of the standard boiling point of the extraction solvent, the temperature difference is preferably of a degree such that the extraction solvent can be separated from the compound to be separated in the present invention by simple distillation, stripping, or the like; i.e., the temperature difference is usually 20° C. or more. However, if the standard boiling point is too high, the extraction solvent itself may be decomposed. Thus, the specific range of the standard boiling point of the extraction solvent is preferably 30 to 150° C., and more preferably 30 to 80° C.

The amount of the extraction solvent used in the present invention is not limited. Since high efficiency is attained when the proportion of the extraction solvent to be used relative to the starting material (composition containing hexafluorobutadiene and an additional compound) is high (i.e., the concentration of the extraction solvent is high), the extraction solvent is, for example, preferably contained in an amount of 0.1 to 100 mol, more preferably 0.5 to 50 mol, and still more preferably 1 to 20 mol, per mol of the starting material (composition containing hexafluorobutadiene and an additional compound).

The separation method of the present invention can be carried out, for example, by introducing a composition F11 containing hexafluorobutadiene and an additional compound into a distillation column T1, and performing extractive distillation in the distillation column T1 to recover hexafluorobutadiene S11, as shown in FIG. 1. However, it is also possible to provide a solvent recovery column T2 at the downstream side of the distillation column T1, and recover the extraction solvent S14 and reuse the extraction solvent S14 in the distillation column T1. In this case, the number of plates of the distillation column T1 and the solvent recovery column T2 can be appropriately selected by examining, in a preliminary manner, the relationship of the purity of a distillate component, the recovery rate, and the like. FIG. 1 shows an example in which an extraction solvent having a relative volatility greater than 1 is used. Even when an extraction solvent having a relative volatility of less than 1 is used, separation can be performed in the same manner; however, there is a difference in that the material recovered in the distillation column T1 is hexafluorobutadiene or an additional compound.

Operation conditions such as the temperature in each part of the distillation column T1 and the solvent recovery column T2, the plate in which the starting material is supplied, and the supply amount of the extraction solvent are not limited. However, the operation conditions vary depending on the performance of the distillation column T1 and the solvent recovery column T2, the content ratio of the hexafluorobutadiene in the non-treated product (starting material) to the additional compound, the type and amount of the extraction solvent to be used, or the like. These conditions can be determined by conducting preliminary tests. In addition, the extraction solvent can be added to the starting material in order to keep distillation operation stable. The method of the present invention can be carried out by a discontinuous operation, or by a continuous operation; the method is preferably performed by a continuous operation from an industrial viewpoint. Moreover, by increasing the number of theoretical plates of the extractive distillation column, and by actually increasing the number of columns, the distillate component can be further purified. In the product recovery stream, a demister for removing the extraction solvent that may be entrained in a very small amount, or a solvent removal column filled with an adsorbent such as activated carbon or molecular sieve, may be provided.

The reactor used in the present invention is preferably made of carbon steel lined with at least one of glass, stainless steel, ethylene tetrafluoride resin, chlorotrifluoroethylene resin, vinylidene fluoride resin, PFA resin, etc.

Hexafluorobutadiene Composition

Thus, the hexafluorobutadiene can be obtained with high purity; this also enables the obtainment of a hexafluorobutadiene composition in which the content of the additional compound is less than 0.1 mol % (particularly 0.001 to 0.05 mol %, more preferably 0.001 to 0.01 mol %), per 100 mol % of the total amount of the hexafluorobutadiene composition. This hexafluorobutadiene composition can also be obtained as an azeotropic or an azeotropic-like composition. For example, a composition composed of hexafluorobutadiene and 0.05 mol; of $CF_3CF\!=\!CHCF_3$ ($C_4F_7H$) has a gas phase composition of 99.95% and a liquid phase composition of 99.95% at a pressure of 0.05 MPaG and 15.7° C.

Such a hexafluorobutadiene composition of the present invention can be efficiently used for various purposes, including etching gases for forming state-of-the-art microstructures such as semiconductors and liquid crystals; refrigerants; heat transfer media; foaming agents; resin monomers; etc.

EXAMPLES

The features of the present invention are clarified with reference to the Examples shown below. The present invention is not limited to these Examples.

Reference Example 1

An eggplant flask with a condenser, to which a trap is connected, was cooled to −78° C.; and 40 g (0.16 mol) of xylene, 7.25 g (0.12 mol) of zinc, and 20 g (0.05 mol) of a starting material ($ClCF_2CFClCF_2CF_2I$) were added to the eggplant flask. The mixture was heated under stirring until the inside temperature reached 140° C. After the inside temperature became constant, N,N-dimethylformamide (DMF) was added dropwise under reflux at a dropwise addition rate of 0.04 mol/hour (0.8 mol/hour per mol of the starting material ($ClCF_2CFClCF_2CF_2I$)) for 1 hour, and heating reflux was continued while stirring. After the completion of the reaction, a liquid collected in the trap was analyzed by gas chromatography. The results showed that the amount of $CF_2{=}CFCF{=}CF_2$ was 89 mol %, the amount of $CF_2{=}CFCF_2CF_2H$ was 3 mol %, and the amount of other additional compounds (octafluoro-1-butene, octafluoro-2-butene, heptafluoro-1-butene other than $CF_2{=}CFCF_2CF_2H$, heptafluoro-2-butene, etc.) was 8 mol % in total. Specifically, the amount of the additional compounds was 11 mol %.

Reference Example 2

Treatment was performed in the same manner as in Reference Example 1, except that $ICF_7CF_2CF_2CF_2I$ was used as a starting material (substrate) in place of $ClCF_2CFClCF_2CF_2I$. After the completion of the reaction, a liquid collected in the trap was analyzed by gas chromatography. The results showed that the amount of $CF_2{=}CFCF{=}CF_2$ was 73 mol %, the amount of $CF_2{=}CFCF_2CF_2H$ was 20 mol %, the amount of other additional compounds (octafluoro-1-butene, octafluoro-2-butene, heptafluoro-1-butene other than $CF_2{=}CFCF_2CF_2H$, heptafluoro-2-butene, etc.) was 2 moil, and the amount of other side product was 5 mol %. Specifically, the amount of the additional compounds was 22 mol %.

Reference Example 3

The following solvents were individually added to the crude of the hexafluorobutadiene obtained in Reference Example 1 (hereinafter, sometimes referred to as "$C_4F_6$"). By observing change in concentration of the side product ($CF_3CF{=}CHCF_3$, hereinafter, sometimes referred to as "$C_4F_7H$"), each solvent was confirmed for whether it had an effect as an extraction solvent. Table 1 below shows the results obtained by calculating the relative volatility of hexafluorobutadiene and $CF_3CF{=}CHCF_3$ from the results of the gas-liquid equilibrium. In order to use a solvent as an extraction solvent, the specific volatility must be far from 1. It can be understood from the results of Table 1 that all of ethylene glycol monomethyl ether, perchloroethylene (tetrachloroethylene), methanol, ethanol, and methyl ethyl ketone can be used as extraction solvents; and that hexafluorobutadiene can be obtained with high purity.

TABLE 1

| Solvent | Specific volatility |
|---|---|
| None | 1.05 |
| Ethylene glycol monomethyl ether | 1.11 |
| Perchloroethylene | 0.68 |
| Methanol | 1.30 |
| Ethanol | 1.50 |
| MEK (Methyl ethyl ketone) | 1.70 |

Example 1

Simulation evaluation was performed on the separation method of the present invention.

An extractive distillation process was established using methanol as an extraction solvent. Methanol was added in a 4-fold molar amount relative to that of the crude of hexafluorobutadiene. Hexafluorobutadiene containing 500 ppm of $C_4F_7H$ was subjected to the extractive distillation step to separate $C_4F_7H$ from hexafluorobutadiene.

FIG. 1 shows the outline of the process. The theoretical plate number of the distillation column is 14 for the extractive distillation column T1, and 8 for the solvent recovery column T2. The extractive distillation column and the solvent recovery column both had an operation pressure of 0.05 MPaG (G means gauge pressure). The still temperature was 72.4° C. for the extractive distillation column, and 75.1° C. for the solvent recovery column.

Table 2 below shows the material balance.

TABLE 2

| | F11 | S11 | S12 | S13 | S14 |
|---|---|---|---|---|---|
| | Mol flow rate (kmol/hr) | | | | |
| $C_4F_6$ | 0.0857 | 0.08566 | 8.57E−05 | 8.57E−05 | 0 |
| $C_4F_7H$ | 3.82E−05 | 3.82E−08 | 3.81E−05 | 3.81E−05 | 0 |
| Methanol | 0 | 8.09E−07 | 0.139 | 1.39E−05 | 0.139 |
| | Mol composition | | | | |
| $C_4F_6$ | 99.95 | 99.99 | 0.06 | 62.24 | 0 |
| $C_4F_7H$ | 0.05 | 40 ppm | 0.03 | 27.69 | 0 |
| Methanol | 0 | 0 | 99.91 | 10.07 | 100 |

Comparative Example 1

Calculation was performed for the case in which hexafluorobutadiene containing 500 ppm of $C_4F_7H$ as an impurity was separated only by common distillation, without using the extractive distillation step.

It was found that a distillation column having a theoretical plate number of 120 was needed to achieve 4N purity and the same product recovery rate as in Example 1.

Thus, regardless of which solvent was used, a desired purity of 99.99% or more (4N) could be achieved by extractive distillation using equipment surprisingly smaller than that used for common distillation.

Example 2

Under the etching conditions of ICP (Inductive Coupled Plasma) discharge power: 600 W, bias power: 200 W, pressure: 3 mTorr (0.399 Pa), electron density: $8{\times}10^{10}$ to $2{\times}10^{11}$ cm$^{-3}$, and electron temperature: 5 to 7 eV, a semiconductor substrate having an $SiO_2$ film with a thickness of about 1 μm on an Si substrate and a resist pattern with a 0.21

µm-diameter hole thereon was etched using cyclic $C_4F_8$ (conventional product) or $C_4F_6$ (structure: $CF_2=CFCF=CF_2$) produced in Reference Example 1. Table 3 below shows the rate and selectivity in the etching.

$C_4F_6$ (structure: $CF_2=CFCF=CF_2$) had higher selectivity relative to resist for electron beam lithography and higher selectivity relative to silicon than those of c-$C_4F_8$.

TABLE 3

| Gas | $SiO_2$ etching rate Å/min | Resist etching rate Å/min | Selectivity relative to resist $SiO_2$/Resist | Si etching rate Å/min | Selectivity relative to silicon $SiO_2$/Si |
|---|---|---|---|---|---|
| c-$C_4F_8$ (Conventional product) | 6776 | 5061 | 1.34 | 2748 | 2.47 |
| $C_4F_6$ | 5470 | 2442 | 2.24 | 870 | 6.29 |

The invention claimed is:

1. A method for producing hexafluorobutadiene, comprising a step of subjecting a starting material composition containing hexafluorobutadiene and at least one additional compound selected from the group consisting of octafluoro-1-butene, octafluoro-2-butene, and heptafluoro-2-butene to extractive distillation in the presence of an extraction solvent to reduce the concentration of the additional compound.

2. The production method according to claim 1, wherein the extraction solvent contains at least one compound selected from the group consisting of oxygen-containing hydrocarbons and halogen-containing hydrocarbons.

3. A method for separating hexafluorobutadiene and at least one additional compound selected from the group consisting of octafluoro-1-butene, octafluoro-2-butene, and heptafluoro-2-butene, the method comprising a step of subjecting a composition containing hexafluorobutadiene and the additional compound to extractive distillation in the presence of an extraction solvent.

4. The method according to claim 3, wherein the extraction solvent contains at least one compound selected from the group consisting of oxygen-containing hydrocarbons and halogen-containing hydrocarbons.

5. A composition containing hexafluorobutadiene and at least one additional compound selected from the group consisting of octafluoro-1-butene, octafluoro-2-butene, and heptafluoro-2-butene, wherein the additional compound is contained in an amount of less than 0.1 mol % per 100 mol % of the total amount of the composition.

6. An azeotropic composition containing hexafluorobutadiene and at least one additional compound selected from the group consisting of octafluoro-1-butene, octafluoro-2-butene, and heptafluoro-2-butene.

7. The composition according to claim 5, for use in an etching gas, a refrigerant, a heat transfer medium, a foaming agent, or a resin monomer.

8. The composition according to claim 6, for use in an etching gas, a refrigerant, a heat transfer medium, a foaming agent, or a resin monomer.

* * * * *